US008956360B2

(12) United States Patent
Boachie-Adjei et al.

(10) Patent No.: US 8,956,360 B2
(45) Date of Patent: Feb. 17, 2015

(54) DEVICES, SYSTEMS, AND METHODS FOR PERFORMING SPINAL SURGERY

(75) Inventors: Oheneba Boachie-Adjei, Briarcliff, NY (US); John Kish, Pennsauken, NJ (US); Craig Kashuba, Exton, PA (US); Jennifer Moore, Summit Point, WV (US); Michael Barrus, Ashburn, VA (US); Nicholas A. Psaltos, Purcellville, VA (US)

(73) Assignee: K2M, Inc., Leesburg, VA (US)

( * ) Notice: Subject to any disclaimer, the term of this patent is extended or adjusted under 35 U.S.C. 154(b) by 335 days.

(21) Appl. No.: 13/251,671

(22) Filed: Oct. 3, 2011

(65) Prior Publication Data

US 2012/0083853 A1    Apr. 5, 2012

Related U.S. Application Data

(60) Provisional application No. 61/388,704, filed on Oct. 1, 2010.

(51) Int. Cl.
*A61B 17/88* (2006.01)
*A61B 17/70* (2006.01)

(52) U.S. Cl.
CPC ......... *A61B 17/7086* (2013.01); *A61B 17/7038* (2013.01); *A61B 17/7077* (2013.01); *A61B 17/7037* (2013.01)
USPC ....................................... 606/86 A

(58) Field of Classification Search
CPC .................... A61B 17/88; A61B 17/8872
USPC ................. 606/86 A, 86 R, 914, 90
See application file for complete search history.

(56) References Cited

U.S. PATENT DOCUMENTS

| 5,513,827 | A   |     5/1996 | Michelson |
| 7,794,464 | B2* |     9/2010 | Bridwell et al. ........... 606/86 A |
| 8,221,426 | B2* |     7/2012 | Justis et al. ................ 606/86 A |
| 2002/0052603 | A1 |     5/2002 | Nichols et al. |
| 2006/0025769 | A1 |     2/2006 | Dick et al. |
| 2006/0271050 | A1 |    11/2006 | Piza Vallespir |
| 2007/0093817 | A1 |     4/2007 | Barrus et al. |
| 2007/0213716 | A1 |     9/2007 | Lenke et al. |

(Continued)

FOREIGN PATENT DOCUMENTS

WO    2009158707 A1    12/2009

OTHER PUBLICATIONS

International Search Report from PCT/US2011/054582 mailed Feb. 8, 2012.

*Primary Examiner* — Eduardo C Robert
*Assistant Examiner* — Julianna N Harvey
(74) *Attorney, Agent, or Firm* — Carter DeLuca Farrell & Schmidt LLP

(57) ABSTRACT

A manipulation device includes a body portion, a plurality of articulatable legs, and at least one lock member. The legs extend from the body portion. Each of the legs is configured to engage a surgical instrument at a distal end thereof. Each of the legs is transitionable between an unlocked condition, wherein the leg is free to articulate, and a locked condition, wherein the leg is fixed in position. The at least one lock member is operably disposed within the body portion and is coupled to at least one of the articulatable legs. The lock member is rotatable relative to the body portion between an unlocked position and a locked position for transitioning the at least one articulatable leg coupled thereto between the unlocked condition and the locked condition.

20 Claims, 14 Drawing Sheets

(56) References Cited

U.S. PATENT DOCUMENTS

| | | |
|---|---|---|
| 2007/0277815 A1* | 12/2007 | Ravikumar et al. .......... 128/99.1 |
| 2008/0077138 A1* | 3/2008 | Cohen et al. .................... 606/61 |
| 2009/0018593 A1 | 1/2009 | Barrus et al. |
| 2009/0062858 A1* | 3/2009 | Dziedzic et al. .............. 606/278 |
| 2011/0106082 A1* | 5/2011 | Kave et al. ...................... 606/70 |
| 2011/0172714 A1 | 7/2011 | Boachie-Adjei et al. |
| 2012/0197297 A1* | 8/2012 | Bootwala et al. ............. 606/246 |

* cited by examiner

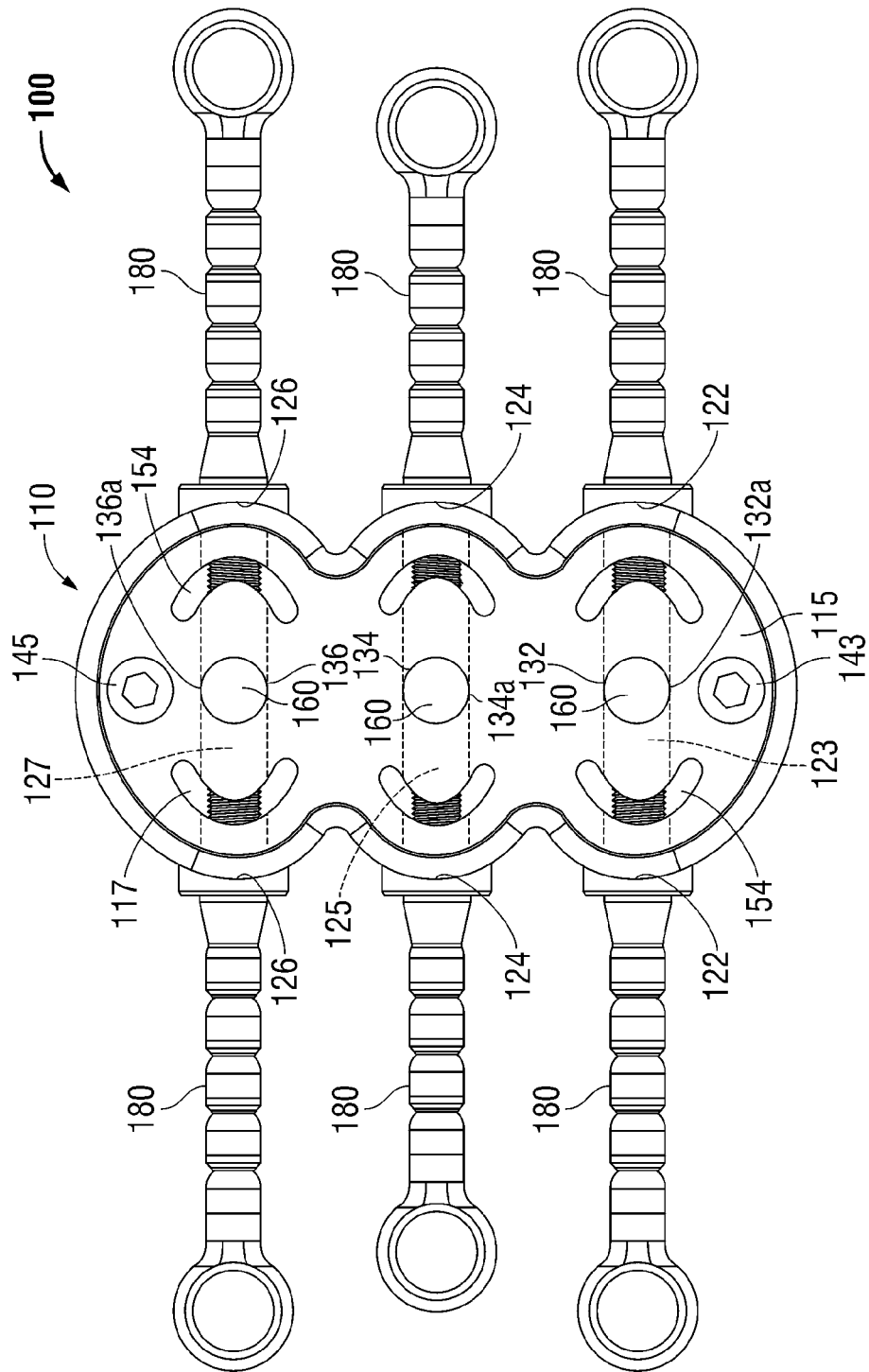

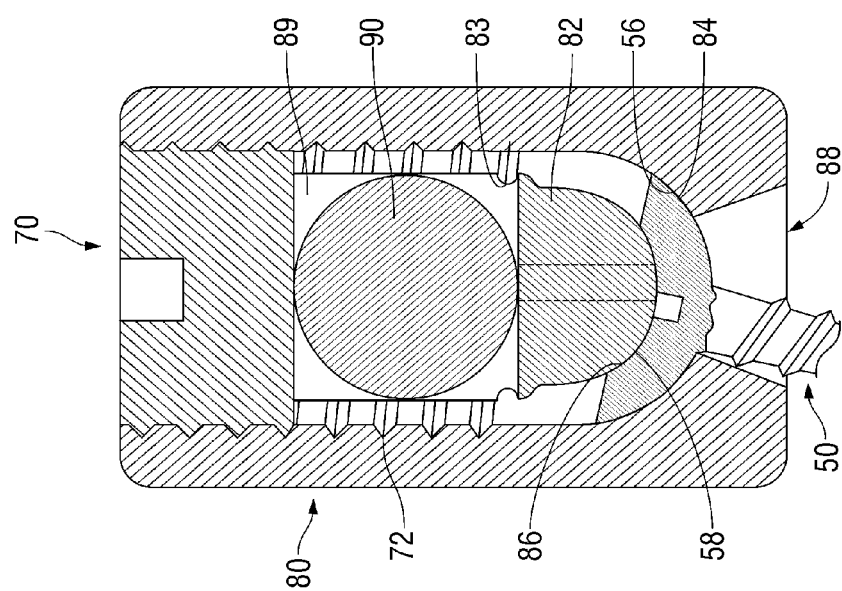
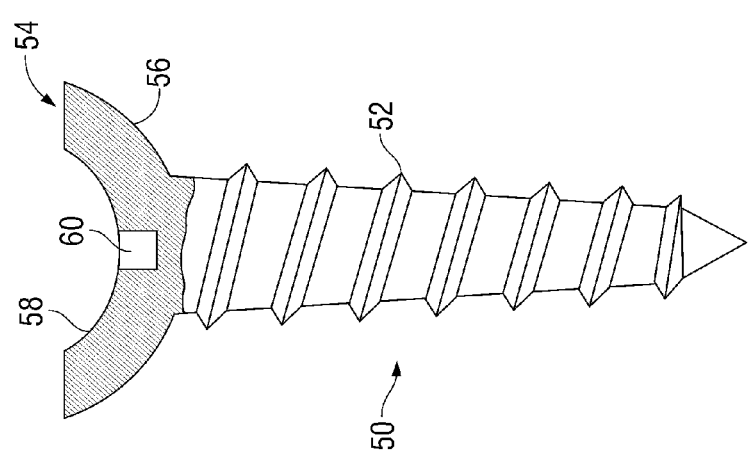

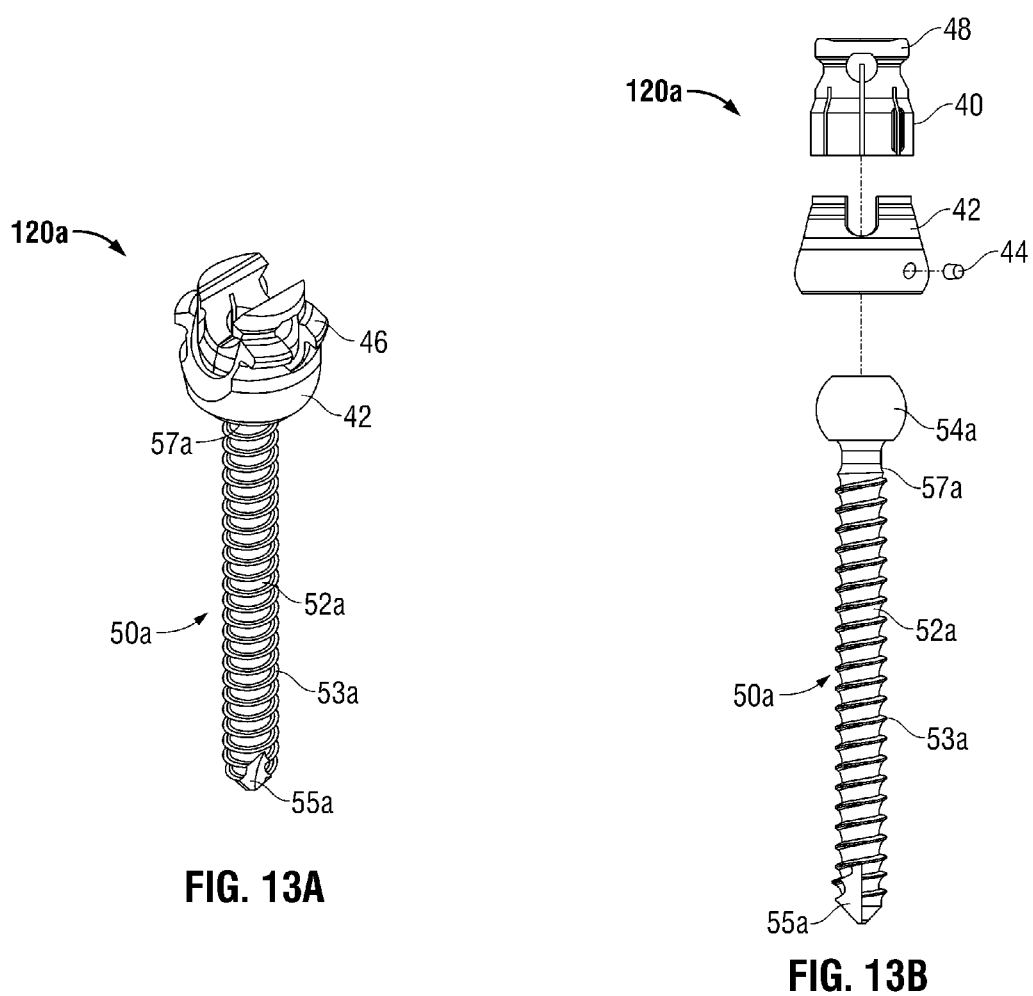

DEVICES, SYSTEMS, AND METHODS FOR PERFORMING SPINAL SURGERY

CROSS-REFERENCE TO RELATED APPLICATIONS

This application claims priority to, and the benefit of, U.S. Provisional Patent Application No. 61/388,704, filed on Oct. 1, 2010, the entire contents of which are hereby incorporated by reference herein.

BACKGROUND

1. Technical Field

The present disclosure relates to orthopedic surgery and, more particularly, to devices, systems, and methods for performing spinal surgery.

2. Background of Related Art

The correction of spinal deformities often requires stabilization and fixation of vertebrae in a particular spatial relationship. Typically, a plurality of bone pins, anchors, cables, hooks, or screws are placed in the vertebrae and are interconnected by one or more spinal rods to maintain a predetermined spatial relationship between the vertebrae. Such devices may be permanently implanted in the subject or, alternatively, may subsequently be removed when no longer needed.

Certain deformities of the spinal column, e.g., severe scoliosis of the spine, require considerable correction. The use of conventional devices for such spinal correction procedures may necessitate prolonged surgery and/or a series of separate surgeries. For example, positioning and connecting rigid screws and connecting rods using conventional instrumentation requires multiple connecting and positioning steps in order to stabilize and fixate the vertebrae in the desired position. These steps may be performed during a single, prolonged surgery, or, in some cases, may need to be broken up into a series of separate surgeries.

Further, conventional rigid screws and connecting rods do not provide any degree of flexibility, thus making manipulation and/or repositioning of the spinal vertebrae prior to locking the connecting rods and screws to one another more difficult. More recently, in an attempt to facilitate the introduction and locking of the connecting rods and screws when building a spinal construct, polyaxial screws have been employed. However, while these polyaxial screws may facilitate attachment of the connecting rod thereto, polyaxial screws and other similar flexible connections may provide too great a range of motion for use in procedures that require the range of motion to be restricted to only uniplanar or monoaxial movement of the connecting rod relative to the screw.

SUMMARY

In accordance with one embodiment of the present disclosure, a manipulation device is provided. The manipulation device includes a body portion, a plurality of articulatable legs extending from the body portion, and at least one lock member operably disposed within the body portion. Each of the articulatable legs is configured to engage a surgical instrument at a distal end thereof and is transitionable between an unlocked condition, wherein the articulatable leg is free to articulate, and a locked condition, wherein the articulatable leg is fixed in position. The lock member(s) is coupled to one or more of the articulatable legs and is rotatable relative to the body portion between an unlocked position and a locked position for transitioning the articulatable leg(s) coupled thereto between the unlocked condition and the locked condition.

In embodiments, the lock member is coupled to a pair of articulatable legs such that rotation of the lock member between the locked position and the unlocked position transitions both articulatable legs of the pair between the unlocked condition and the locked condition.

In embodiments, each of the articulatable legs includes a cable coupled to the lock member at a proximal end thereof, a distal connector coupled to the cable at a distal end thereof and configured to engage a surgical instrument therein, and a plurality of alternating male and female linkages disposed about the cable between the proximal and distal ends thereof.

In embodiments, the cable is transitionable between a substantially un-tensioned state and a substantially tensioned state to transition the articulatable leg between the unlocked condition and the locked condition. More specifically, in the substantially un tensioned state, the alternating male and female linkages are free to articulate relative to one another. In the substantially tensioned state, on the other hand, the alternating male and female linkages are retained in fixed position relative to one another.

In embodiments, each articulatable leg further includes an adjustment ring coupled thereto that is selectively rotatable relative to the articulatable leg to vary the tension on the cable.

In embodiments, the manipulation device further includes a handle portion coupled to the body portion. The handle portion may be releasably engagable with the body portion.

In embodiments, the lock member includes an engagement recess defined therein that is configured to receive a complementary engagement tool for rotating the lock member between the unlocked position and the locked position.

In embodiments, the body portion includes at least one compression relief slot defined therein.

A method of performing spinal surgery is also provided in accordance with the present disclosure. The method includes providing a manipulation device including a body portion and a plurality of articulatable legs extending from the body portion (or according to any of the embodiments above), engaging a surgical instrument to each of the articulatable legs, manipulating at least one of the surgical instruments independently of the other surgical instruments, locking the plurality of articulatable legs to fixedly retain each of the surgical instruments in position relative to one another and relative to the body portion, and manipulating the body portion to manipulate the surgical instruments in coordination with one another.

In embodiments, the method further includes engaging each of the surgical instruments to a bone screw engaged within a vertebrae, manipulating at least one of the surgical instruments to align the vertebrae, fixedly retaining the vertebrae in alignment with one another, and manipulating the vertebrae in coordination with one another. The method may further include reducing a spinal rod into one or more of the bone screws and locking the spinal rod within the bone screws.

In embodiments, the method further includes rotating a lock member from an unlocked position to a locked position to lock at least one of the articulatable legs coupled thereto.

A surgical system is also provided in accordance with the present disclosure. The surgical system includes a manipulation device according to any of the embodiments above and a surgical instrument engaged to each of the articulatable legs of the manipulation device such that, in the unlocked condition, the surgical instruments are manipulatable independently of one another and such that, in the locked condition, the surgical instruments are manipulatable in coordination with one another.

In embodiments, one or more of the surgical instruments is a manipulator. Alternatively or additionally, one or more of the surgical instruments may be a rod reduction device.

BRIEF DESCRIPTION OF THE DRAWINGS

Embodiments of the present disclosure are described herein with reference to the accompanying drawings, wherein:

FIG. 2C is a bottom view of the manipulation device of FIG. 2A;

FIG. 12A is a side view of an embodiment of a bone screw usable with the presently disclosed surgical systems;

FIG. 12B is a side cross-sectional view of a coupling element with the bone screw of FIG. 12A and a spinal rod;

FIG. 13A is a perspective view of an alternate embodiment of a bone screw usable with the presently disclosed surgical systems;

FIG. 13B is an exploded view, with parts separated, of the bone screw of FIG. 13A;

DETAILED DESCRIPTION

Figure 1:
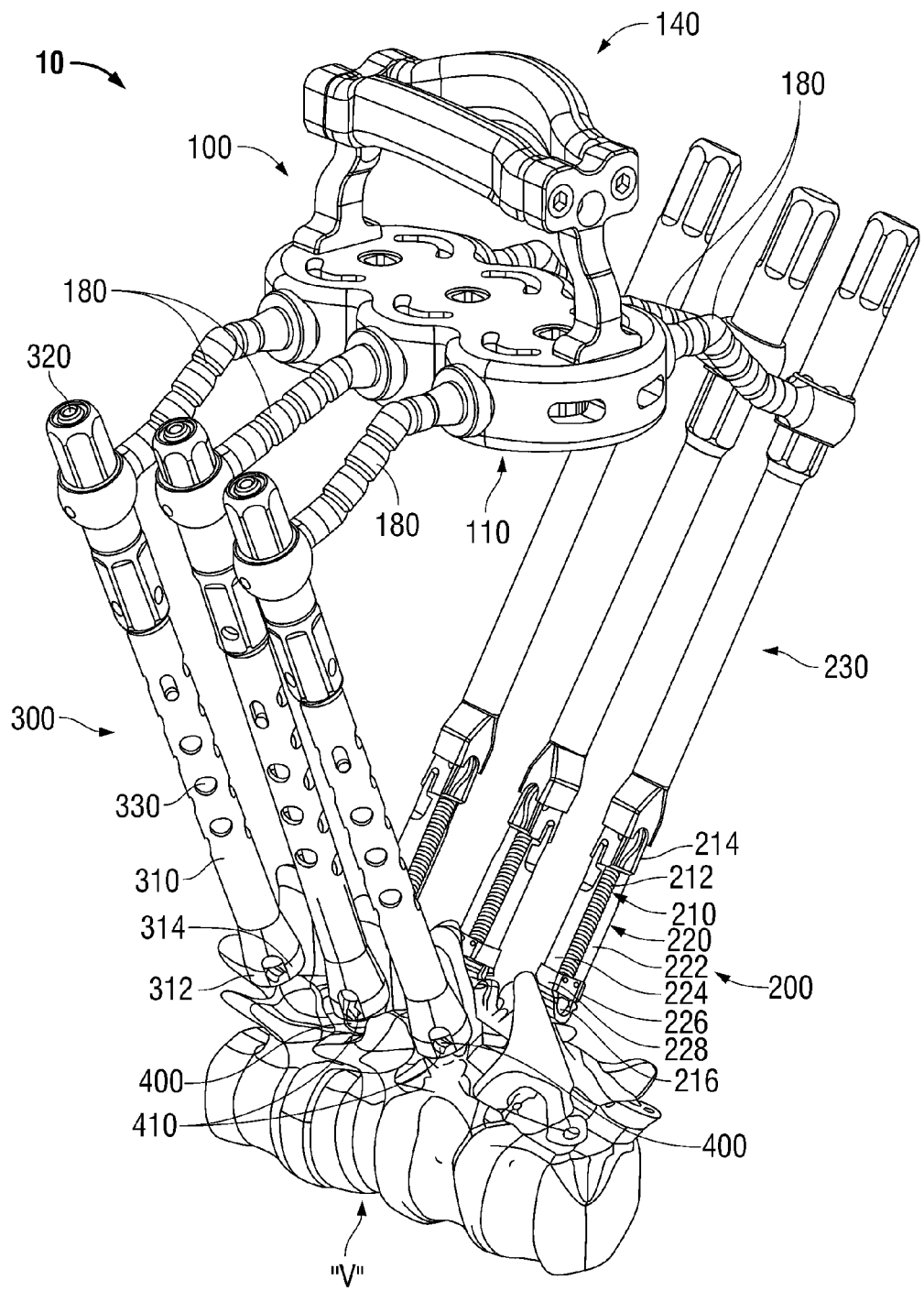
FIG. 1 is a perspective view of one embodiment of a surgical system provided in accordance with the present disclosure and shown in use during a spinal surgical procedure.

Various embodiments of the present disclosure will now be described in detail with reference to the drawings, wherein like reference numerals identify similar or identical elements.

In the drawings and in the description that follows, the term "proximal," will refer to the end of a device or system that is closest to the operator, while the term "distal" will refer to the end of the device or system that is farthest from the operator. In addition, the term "cephalad" is used to indicate a direction toward a patient's head, whereas the term "caudad" indicates a direction toward the patient's feet. Further still, the term "medial" indicates a direction toward the middle of the body of the patient, whilst the term "lateral" indicates a direction toward a side of the body of the patient (i.e., away from the middle of the body of the patient). The term "posterior" indicates a direction toward the patient's back, and the term "anterior" indicates a direction toward the patient's front. In the following description, well known functions or constructions are not described in detail to avoid obscuring the present disclosure in unnecessary detail.

Turning now to FIG. 1, a surgical system for use in performing spinal surgery is shown generally identified by reference numeral 10. Surgical system 10 generally includes a plurality of surgical instruments, e.g., one or more rod reduction devices 200 and/or one or more manipulators 300, configured for performing one or more spinal surgical procedures, and a manipulation device 120b configured to retain each of the surgical instruments in a desired position relative to one another and to manipulation device 100. Manipulation device 120b generally includes a body portion 110, a handle portion 140 engaged to and extending from body portion 110, and a plurality of articulatable legs 180 disposed about and extending from body portion 110 that are each configured to engage a surgical instrument. More specifically, each articulatable leg 180, either independently or in conjunction with one or more of the other legs 180, is transitionable between an unlocked condition, wherein the leg 180 is free to articulate relative to body portion 110 and one or more of the other legs 180, and a locked condition, wherein the leg 180 is retained in fixed position relative to body portion 110 and/or one or more of the other legs 180.

Continuing with reference to FIG. 1, as mentioned above, manipulation device 120b may be configured to engage one or more rod reduction devices 200 and/or one or more manipulators 300. Rod reduction devices 200 and manipulators 300 may be used in conjunction with one another and with manipulation device 120b to engage one or more spinal rods 90 (FIG. 12B) to a plurality of bone screws 400 disposed within the vertebrae "V" in a particular configuration. However, although manipulation device 120b is shown and described herein configured for use with rod reduction devices 200 and manipulators 300 to engage one or more spinal rods 90 to a plurality of bone screws 400 disposed within the vertebrae "V," it is envisioned that manipulation device 120b may also be used in conjunction with any other suitable surgical instrument (or instruments) to facilitate performing a wide range of surgical procedures.

Rod reduction device 200 is described in U.S. Patent Application Publication No. 2009/0018593 to Barrus et al., the entire contents of which is hereby incorporated by reference herein, and is one example of a surgical instrument usable with manipulation device 120b during a spinal surgical procedure. Rod reduction device 200 is configured to grasp a head 410 of a bone screw 400 and to control reduction of the spinal rod 90 (FIG. 12B) into a rod receiving recess (not explicitly shown) defined within the head 410 of the bone screw 400. In particular, rod reduction device 200 includes a screwjack mechanism 210 and a grasping fork assembly 220 operably coupled to one another. Screwjack mechanism 210 includes an elongated screw shaft 212 having a controlling member 214 at its proximal end and an anvil, or rod contacting member 216 at its distal end. An elongated rotation tube 230 may be operably engaged to controlling member 214 to facilitate remote operation of controlling member 214. Elongated rotation tube 230 may be configured to be engaged by manipulation device 100, as will be described in greater detail hereinbelow, to retain rod reduction device 200 in a fixed position. Grasping fork assembly 220 includes a pair of grasping members 222, 224, each having a grasping element 226, 228, respectively, disposed at the distal end thereof.

In use, with grasping elements 226, 228 of grasping fork assembly 220 grasping the head 410 of the bone screw 400 therebetween, a drive tool (not shown), or other suitable tool, may be operably engaged to the proximal end of elongated rotation tube 230 and rotated such that corresponding rotation of controlling member 214 is effected. Rotation of controlling member 214, in turn, translates rod contacting member 216 distally to urge the spinal rod 90 (FIG. 12B) distally into the rod receiving recess (not explicitly shown) defined within the head 410 of the bone screw 400.

Manipulator 300 is described in U.S. Patent Application Publication No. 2011/0172714 to Boachie-Adjei et al., the entire contents of which is hereby incorporated by reference herein, and is another example of a surgical instrument usable with manipulation device 120b (and/or rod reduction device 200) during a spinal surgical procedure. Manipulator 300 provides an increased moment arm to facilitate manipulation and repositioning of the bone screw 400 and the spinal rod 90 (FIG. 12B) relative to one another. More specifically, manipulator 300 includes an outer shaft 310, a control knob 320 disposed at a proximal end of outer shaft 310, and an activation rod 330 extending through outer shaft 310. Outer shaft 310 includes a pair of grasping elements 312, 314 disposed at the distal end thereof that are configured to grasp the head 410 of the bone screw 400 therebetween. Activation rod 330 includes a rod contacting element (not shown) disposed at a distal end thereof and is operably coupled to control knob 320 at a proximal end thereof such that rotation of control knob 320 effects longitudinal translation of activation rod 330.

In use, with grasping elements 312, 314 grasping the head 410 of the bone screw 400 therebetween, a drive tool (not shown), or other suitable tool, is operably engaged to control knob 320 and rotated such that activation rod 330 is translated distally. As activation rod 330 is translated distally, the rod contacting element (not shown) contacts the spinal rod 90 (FIG. 12B) and urges the spinal rod 90 (FIG. 12B) (not shown) into the rod receiving recess (not explicitly shown) of the bone screw 400. Further distal translation of activation rod 330, e.g., as a result of further rotation of the drive tool (not shown), may be effected to release the grasping elements 312, 314 from the head 410 of the bone screw 400.

Referring now to FIGS. 2A-2D, as mentioned above, manipulation device 120b generally includes a body portion 110, a handle portion 140 engaged to and extending from body portion 110, and a plurality of articulatable legs 180 disposed about and extending from body portion 110 that are each configured to engage a surgical instrument. Body portion 110 of manipulation device 120b includes a base 112 defining a generally oval shaped configuration, although other configurations are contemplated, and including first and second opposed ends 113a, 113b, respectively, and first and second opposed sides 114a, 114b, respectively. Base 112 further includes a distal surface 115 and an internal cavity 117 defined by opposed ends 113a, 113b, opposed sides 114a, 114b, distal surface 115, and a cover 118, which is configured for engagement within base 112 to substantially enclose internal cavity 117.

A plurality of pairs of leg receiving apertures 122, 124, 126 is defined through base 112 of body portion 110 of manipulation device 100. More specifically, as shown in FIGS. 2A-2D, each side 114a, 114b of base 112 includes three (3) leg receiving apertures 122, 124, 126 defined therethrough. The leg receiving apertures 122, 124, 126 of each side 114a, 114b are aligned with one another to form the three (3) pairs of leg receiving apertures 122, 124, 126: one leg receiving aperture 122, 124, 126 of each pair defined through first opposed side 114a, and the other leg receiving aperture 122, 124, 126 of each pair defined through second opposed side 114b. As such, each pair of leg receiving apertures 122, 124, 126 can be said to define a respective cylindrical volume 123, 125, 127 (that is a portion of internal cavity 117) that extends through internal cavity 117 of body portion 110 between the opposed sides 114a, 114b thereof. Other configurations are also contemplated, e.g., greater or fewer than three (3) pairs of leg receiving apertures 122, 124, 126 may be provided, one or more of the leg receiving apertures 122, 124, 126 may be offset relative to its paired counterpart, one or more of the leg receiving apertures 122, 124, 126 may be unpaired, and/or the leg receiving apertures 122, 124, 126 may be grouped in any other suitable number (e.g., the leg receiving apertures 122, 124, 126 may be grouped in threes, fours, etc.).

With continued reference to FIGS. 2A-2D, a plurality of cam lock member receiving passages 132, 134, 136 is defined through body portion 110 of manipulation device 100. Each cam lock member receiving passage 132, 134, 136 has a first, or distal open end 132a, 134a, 136a defined through distal surface 115 of base 112, and a second, or proximal open end 132b, 134b, 136b defined through cover 118. Each of the cam lock member receiving passages 132, 134, 136 defines a respective cylindrical volume 133, 135, 137 (that is a portion of internal cavity 117) that extends through internal cavity 117 of body portion 110 between distal surface 115 of base 112 and cover 118. Further, each cam lock member receiving passage 132, 134, 136 corresponds to one of the pairs of leg receiving apertures 122, 124, 126, respectively, and is positioned such that cylindrical volumes 123, 125, 127 and respective cylindrical volumes 133, 135, 137 are substantially perpendicular to and substantially intersect one another. That is, cam lock member receiving passage 132 and corresponding leg receiving apertures 122 define perpendicular and intersecting cylindrical volumes 133, 123; cam lock member receiving passage 134 and corresponding leg receiving apertures 124 define perpendicular and intersecting cylindrical volumes 135, 125, respectively; and cam lock member receiving passage 136 and corresponding leg receiving apertures 126 define perpendicular and intersecting cylindrical volumes 137, 127, respectively. As will be described in greater detail below, each articulatable leg 180 is configured to extend through one of the leg receiving apertures 122, 124, 126 and at least partially into the respective cylindrical volume 123, 125, 127 thereof such that a pair of legs 180 may be coupled to each of the cam lock members 160, which are positioned at least partially within the respective intersecting cylindrical volumes 133, 135, 137 defined between the corresponding cam lock member receiving passages 132, 134, 136, respectively.

Handle portion 140 of manipulation device 120b includes a pair of supports 142, 144 engaged to body portion 110 of manipulation device 120b towards respective ends 113a, 113b thereof, although other configurations are also contemplated. In particular, each support 142, 144, is releasably engaged to body portion 110 via a screw 143, 145, respectively, extending through distal surface 115 of base 112, internal cavity 117, cover 118, and into a threaded bore (not shown) defined within the respective support 142, 144. Although other suitable engagement configurations are also contemplated, this screw aperture engagement configuration is advantageous in that it facilitates the installation and interchanging of various different handle portions 140 with body portion 110, e.g., by simply engaging the desired handle portion 140 to body portion 110 via screws 143, 145, or, on other hand, facilitates the use of various different body portions, e.g., body portion 110 or body portion 110' (FIG. 3), with the same handle portion 140.

Handle portion 140 further includes a pair of spaced apart handle members 146, 148 that extend between supports 142, 144. Each handle member 146, 148 is releasably engaged to both supports 142, 144 via screws 147, 149, respectively, and, thus, handle members 146, 148 may be readily interchanged to achieve a desired configuration in accordance with the surgeon's preference, the procedure to be performed, or other factors. For example, a particular size, shape, material, and/or number of handles 146, 148 may be selected and engaged to supports 142, 144 as desired. As can be appreciated, handle portion 140 of manipulation device 120b facilitates the grasping and manipulation of body portion 110 of manipulation device 100. Further, handle members 146, 148 are spaced apart from one another a sufficient distance to permit insertion of an engagement tool (not shown) therebetween and into engagement with any one of the cam lock members 160 to transition one or more pairs or articulatable legs 180 between the unlocked condition and the locked condition.

Continuing with reference to FIGS. 2A-2D, base 112 and/or cover 118 of body portion 110 of manipulation device 120b may also include one or more compression relief slots 152, 154, 156 defined therethrough that function to impart some degree of flexibility, i.e., to reduce the rigidity, of body portion 110. As shown, base 112 and cover 118 each include a pair of compression relief slots 152, 154, respectively, that are symmetrically disposed about the open ends 132a, 134a, 136a and 132b, 134b, 136b, respectively, of cam lock member receiving passages 132, 134, 136. These compression relief slots 152, 154 are configured to absorb some of the torque imparted to body portion 110 in the event of over rotation of one or more of cam lock members 160 and/or to absorb some of the stress imparted to body portion 110 as a result of forces acting one or more of articulatable legs 180, thus helping to inhibit damage to body portion 110. Compression relief slots 156, which are defined through opposed ends 113a, 113b of base 112 of body portion 110 of manipulation device 120b are configured to absorb some of the compressive force resulting from over tightening of screws 143, 145 during engagement of handle portion 140 to body portion 110, thus also helping to inhibit damage to body portion 110. Body portion 110 may further include inwardly bowed areas 158 disposed between each of the leg receiving apertures 122, 124, 126 defined therethrough for relieving some of the stresses imparted to body portion 110.

Figure 2A:
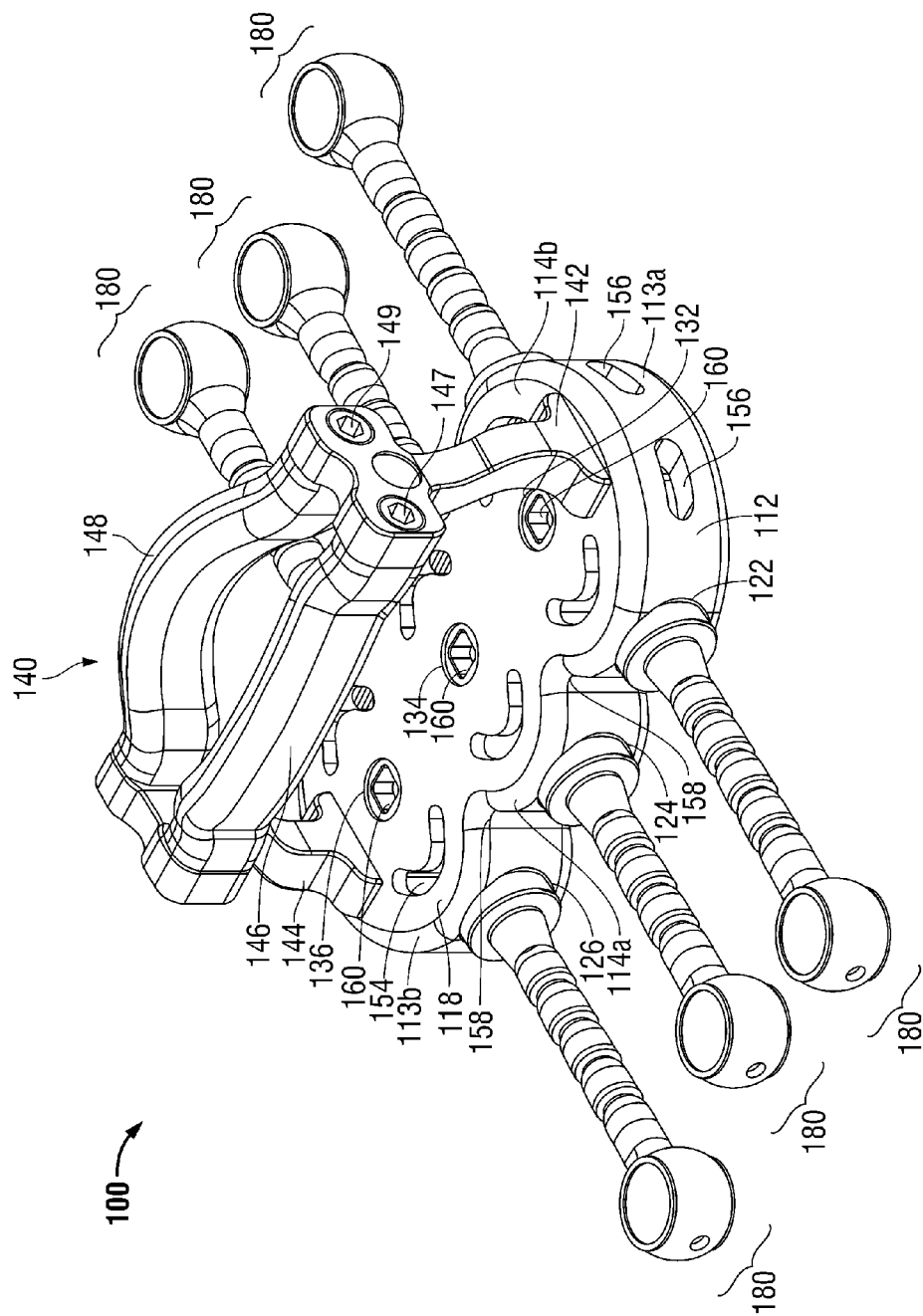
FIG. 2A is a perspective view of a manipulation device of the surgical system of FIG. 1.
Figure 2B:
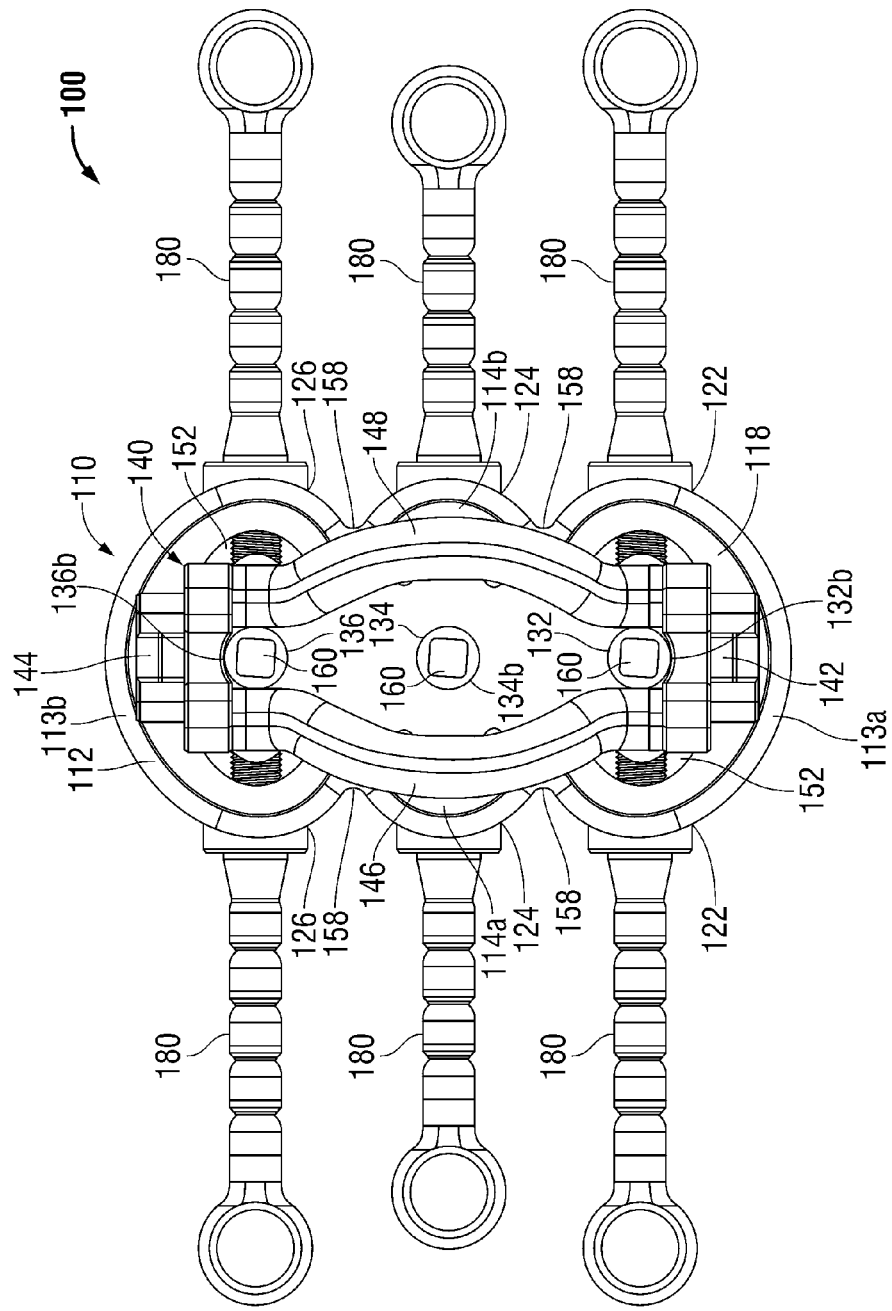
FIG. 2B is a top view of the manipulation device of FIG. 2A.
Figure 2D:
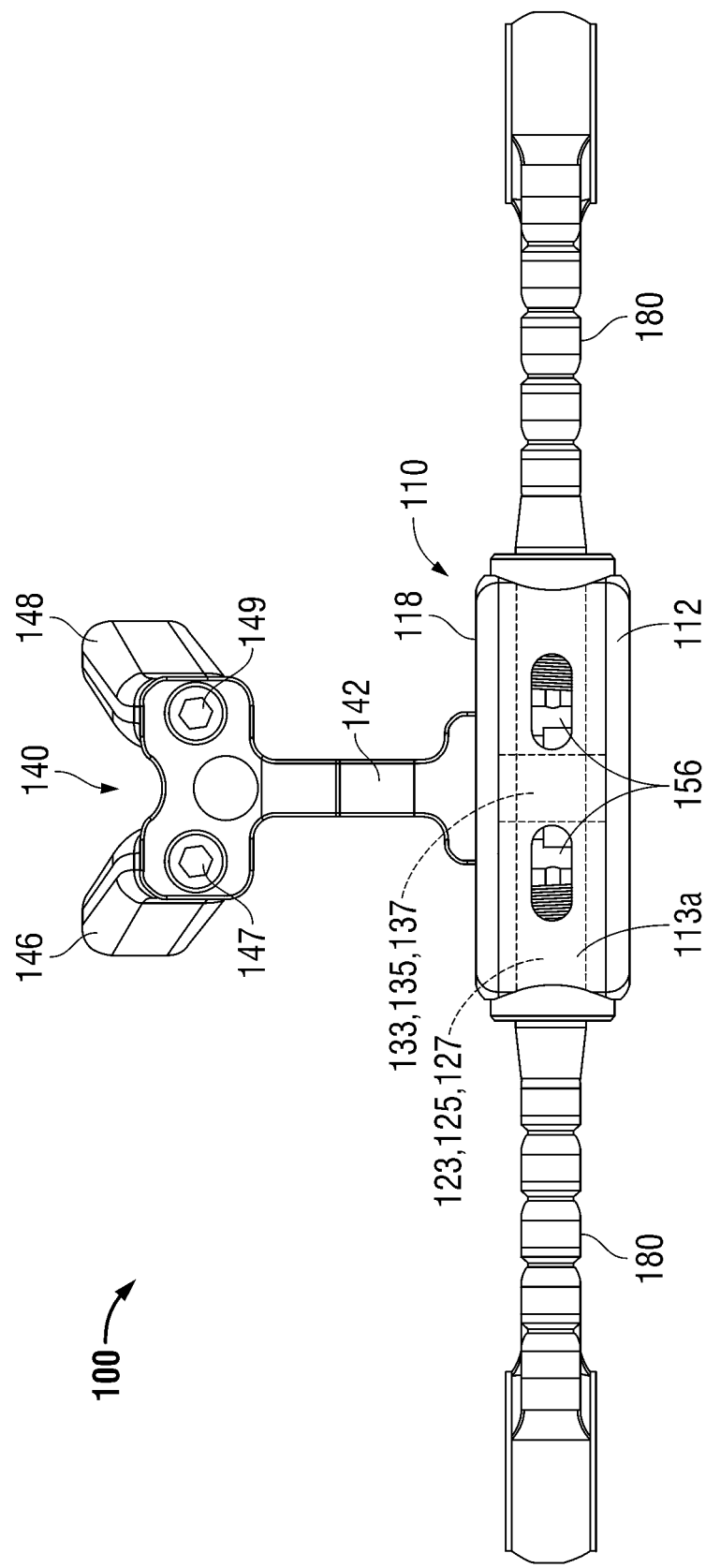
FIG. 2D is an end view of the manipulation device of FIG. 2A.
Figure 3:
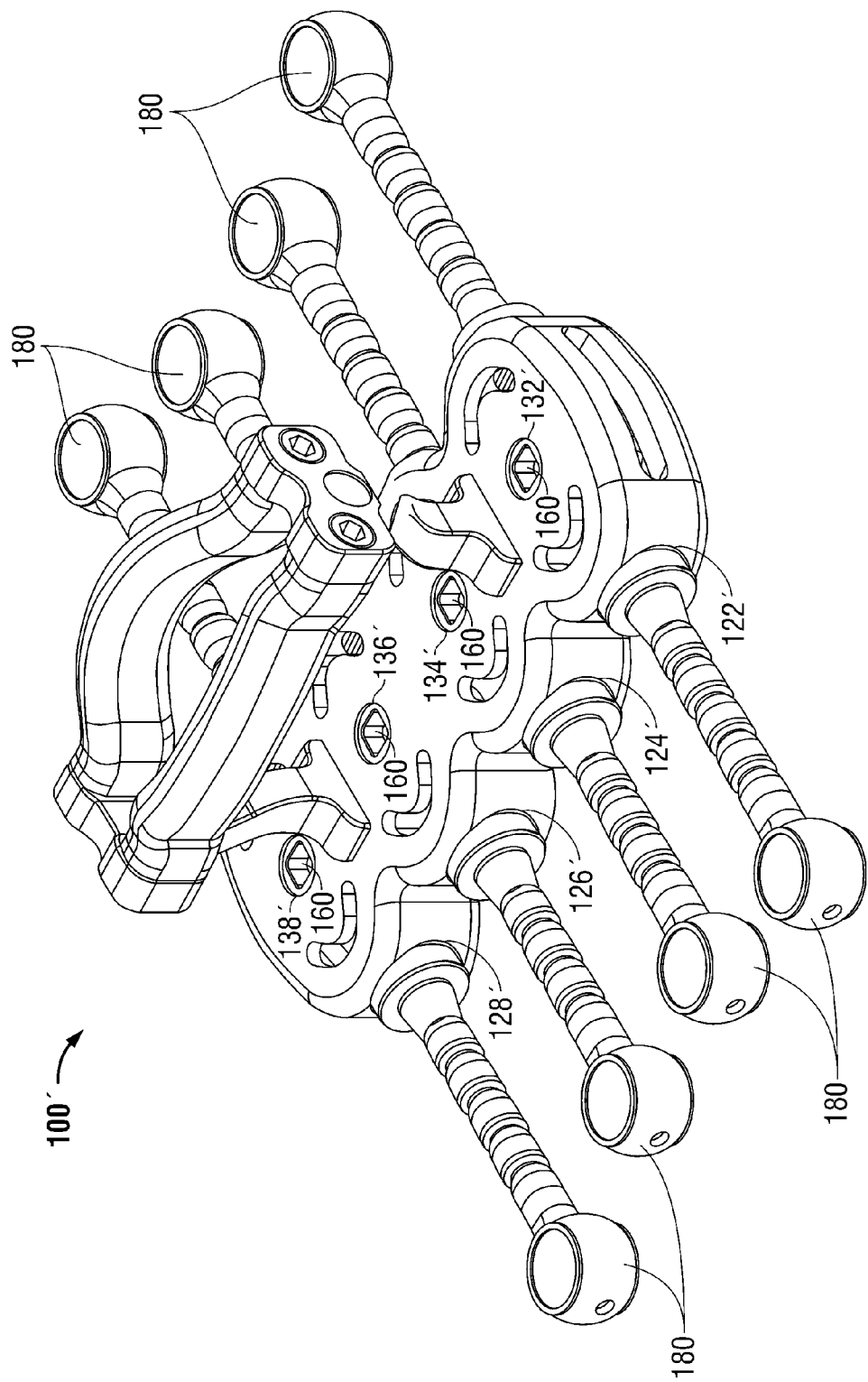
FIG. 3 is a perspective view of another embodiment of a manipulation device configured for use with the surgical system of FIG. 1.

Referring briefly to FIG. 3, another embodiment of a manipulation device is shown generally identified by reference numeral 100'. Manipulation device 100' is substantially similar to manipulation device 120b (FIGS. 1-2D) except that manipulation device 100' includes four (4) pairs of leg receiving apertures 122', 124', 126', 128' (although any suitable number of leg receiving apertures may be provided, depending on the desired number of articulatable legs 180), each of which is configured to receive a pair of articulatable legs 180, and four (4) pairs of corresponding cam lock member receiving passages 132', 134', 136', 138', each of which is configured to receive a cam lock member 160 therein. The components, assembly, use, and operation of manipulation device 100' are otherwise similar to that of manipulation device 120b (FIGS. 1-2D), as will be described in detail below, and, thus, will not be repeated herein for purposes of brevity.

Figure 4:
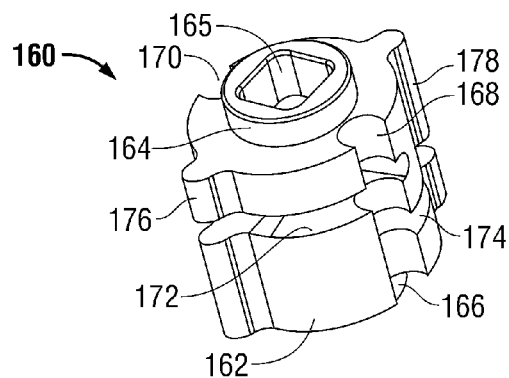
FIG. 4 is a perspective view of a cam lock member of the manipulation device of FIG. 2A.

Turning now to FIG. 4, in conjunction with FIGS. 1-2D, cam lock member 160 is shown. As mentioned above, one cam lock member 160 is configured for positioning at least partially within each of the volumes 133, 135, 137 defined by cam lock member-receiving passages 132, 134, 136, respectively. Each cam lock member 160 is further configured to operably couple to the pair of articulatable legs 180 extending into the corresponding intersecting volume 123, 125, 127 thereof, for transitioning the articulatable legs 180 between the unlocked condition and the locked condition. However, although each cam lock member 160 is configured to engage a pair of articulatable legs 180, it is also envisioned that each cam lock member 160 be coupled to greater fewer than two articulatable legs 180, such that one or more of the cam lock members 160 may be configured to transition any or all of the articulatable legs 180 between the unlocked condition and the locked condition. The cam lock members 160 are substantially similar to one another and, thus, only one will be described hereinbelow.

With continued reference to FIG. 4, in conjunction with FIGS. 1-2D, cam lock member 160 includes a body 162, a proximal cap 164 and a distal cap 166. Proximal and distal caps 164, 166, respectively, are each configured to extend at least partially through the open ends 132a, 134a, 136a and 132b, 134b, 136b, respectively, of the cam lock member receiving passages 132, 134, 136 to rotatably engage cam lock member 160 within body portion 110 of manipulation device 100. Body 162 of cam lock member 160 is configured for positioning within cavity 117 and defines a diameter greater than that of the open ends 132a and 132b, 134a and 134b, 136a and 136b of cam lock member receiving passages 132, 134, 136, respectively, such that body 162 of cam lock member 160 is retained within cavity 117.

Continuing with reference to FIG. 4, in conjunction with FIGS. 1-2D, body 162 of cam lock member 160 includes a pair of opposed longitudinal slots 168, 170 defined therein, each of which is configured to engage an end rod 183 (FIG. 5A) of one of the articulatable legs 180 therein. Body 162 of cam lock member 160 further includes a pair of spaced apart transverse slots 172, 174 extending semi-annularly about the circumference of cam lock member 160. Transverse slots 172, 174 originate from longitudinal slots 168, 170, respectively, such that the cable 181 (FIG. 5A) of each articulatable leg 180 can extend from one of the longitudinal slots 168, 170, wherein it is anchored via end rod 183 (FIG. 5A), and about at least a portion of the circumference of body 162 of cam lock member. A pair of opposed flanges 176, 178 that are equally spaced from opposed longitudinal slots 168, 170 extend outwardly from the outer periphery of body 162 of cam lock member 160.

With continued reference to FIG. 4, in conjunction with FIGS. 1-2D, cam lock member 160 is rotatable relative to body portion 110 of manipulation device 120b between an unlocked position, corresponding to the unlocked condition of the pair of articulatable legs 180 coupled thereto, and a locked position, corresponding to the locked condition of the pair of articulatable legs 180 coupled thereto. In the unlocked position, cam lock member 160 is oriented such that the cables 181 (FIG. 5A) of the articulatable legs 180 coupled thereto are substantially un-tensioned and, thus, the articulatable legs 180 coupled thereto are in the unlocked condition.

Figure 5A:
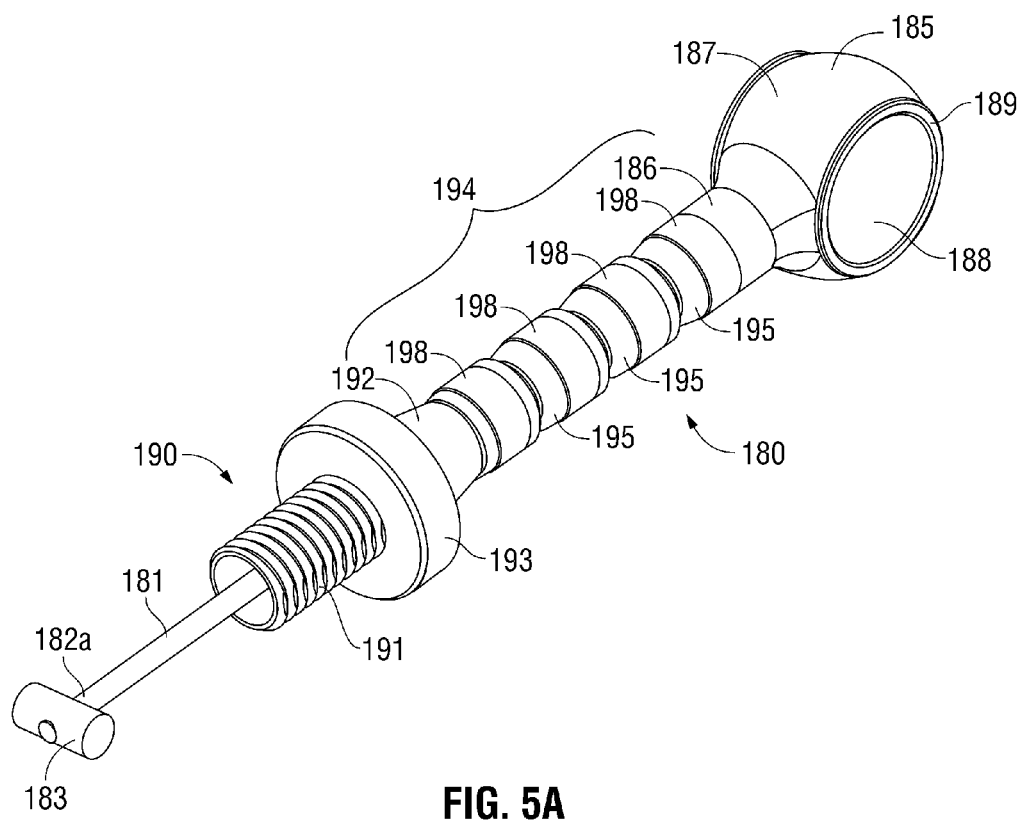
FIG. 5A is a perspective view of one of the legs of the manipulation device of FIG. 2A.
Figure 5B:
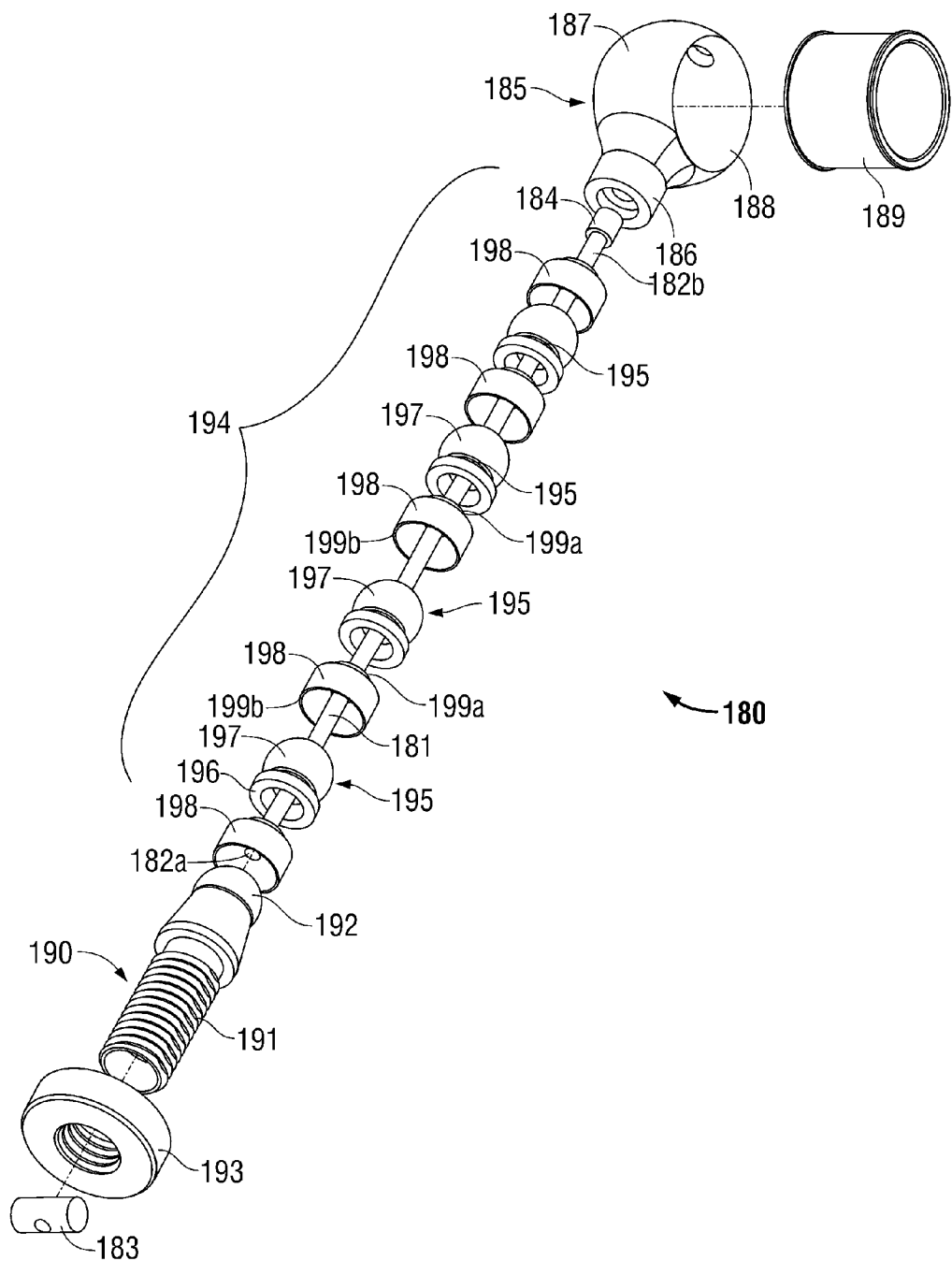
FIG. 5B is an exploded, perspective view of the leg of FIG. 5A.
Figure 6:
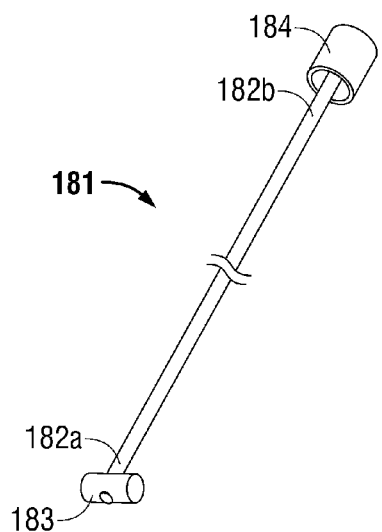
FIG. 6 is a perspective view of a cable of the leg of FIG. 5A.
Figure 7:
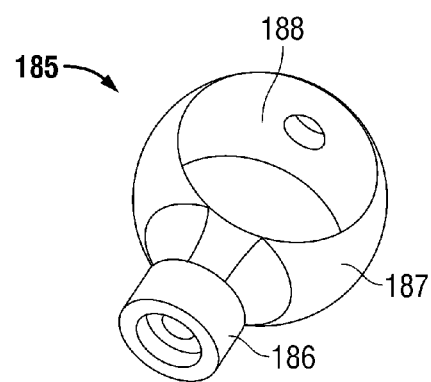
FIG. 7 is a perspective view of a distal connector of the leg of FIG. 5A.
Figure 8:
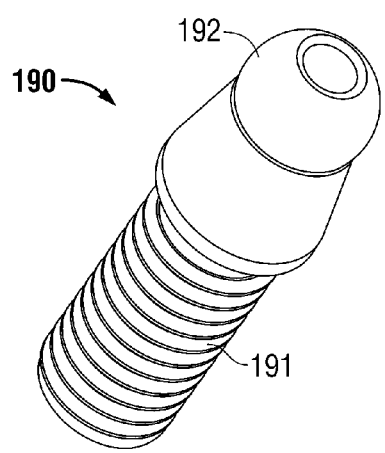
FIG. 8 is a perspective view of a base member of the leg of FIG. 5A.
Figure 9:
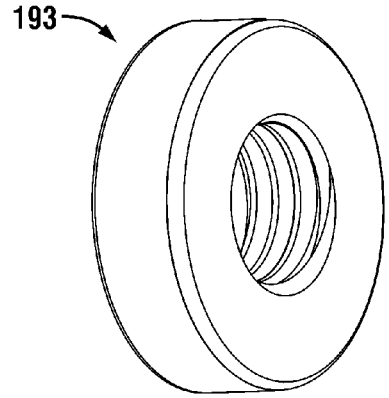
FIG. 9 is a perspective view of an adjustment ring of the leg of FIG. 5A.
Figure 10A:
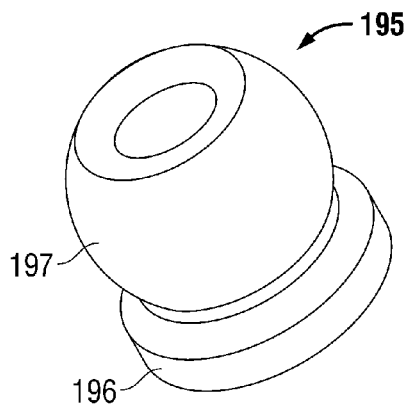
FIG. 10A is a front, perspective view of one of the male linkages of the leg of FIG. 5A.
Figure 10B:
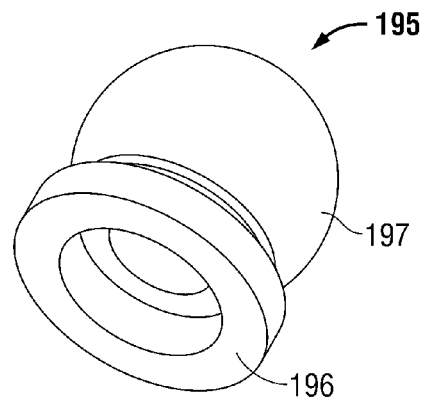
FIG. 10B is a rear, perspective view of the male linkage of FIG. 10A.
Figure 11A:
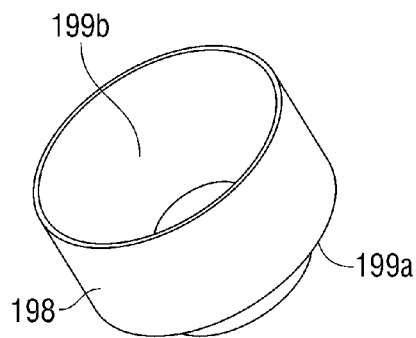
FIG. 11A is a front, perspective view of one of the female linkages of the leg of FIG. 5A.
Figure 11B:
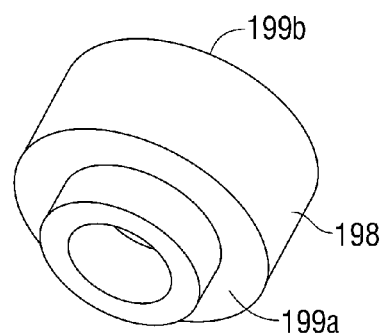
FIG. 11B is a rear, perspective view of the female linkage of FIG. 11A.

In order to transition cam lock member 160 to the locked position, as will be described in greater detail below, cam lock member 160 is rotated such that the cables 181 (FIG. 5A)

coupled there to are at least partially wound up about body 162 of cam lock member 160 (and are disposed at least partially within transverse slots 172, 174), thereby tensioning the cables 181 (FIG. 5A). Upon tensioning of cables 181 (FIG. 5A), the articulatable legs 180 thereof are transitioned from the unlocked condition to the locked condition to fix the position of the articulatable legs 180. Further, upon rotation of cam lock member 160 to the locked position, opposed flanges 176, 178 may be engaged within corresponding internal slots (not explicitly shown) defined within body portion 110 of manipulation device 120b to retain cam lock member 160 in the locked position and, thus, to retain the articulatable legs 180 coupled thereto in the locked condition. Proximal cap 164 of cam lock member 160 (and/or distal cap 166 thereof) may include an engagement recess 165 defined therein that is configured to receive a complementary shaped engagement tool (not shown) for rotating cam lock member 160 between the locked position and the unlocked position and, accordingly, for transitioning the articulatable legs 180 coupled thereto between the unlocked condition and the locked condition.

Turning now to FIGS. 5A-11B, articulatable legs 180 are described. The articulatable legs 180 are substantially similar to one another, except where noted below, and, thus, only one articulatable leg 180 is described hereinbelow to avoid unnecessary repetition.

With continued reference to FIGS. 5A-11B, and to FIGS. 5A-7 in particular, articulatable leg 180 generally includes an elongated cable 181 having a transversely extending end rod 183 engaged at proximal end 182a thereof and a ferrule 184 disposed at distal end 182b thereof. End rod 183, as mentioned above, is configured for engagement within one of the longitudinal slots 168, 170 defined within cam lock member 160 to operably engage articulatable leg 180 and cam lock member 160 to one another. Ferrule 184, on the other hand, is configured to anchor distal end 182b of cable 181 within distal connector 185 of articulatable leg 180. Distal connector 185 includes a neck 186 configured to receive and fixedly engage ferrule 184 therein, and a head 187 that defines a transverse lumen 188 extending therethrough. Transverse lumen 188 is configured to receive a bushing 189 therein that, in turn, is configured to frictionally engage a surgical instrument, e.g., rod reduction device 200 or manipulator 300 (see FIG. 1), therein. Accordingly, bushing 189 may define various different configurations, e.g., a complementary configuration, based on the particular configuration of the surgical instrument to be engaged therein.

Referring to FIGS. 5A-5B, 6 and 8-9, a base member 190 is disposed about cable 181 proximally of and adjacent to end rod 183. Base member 190 includes a lumen extending therethrough that is configured to permit passage of cable 181 therethrough, a threaded proximal shaft 191, and a spherical distal head 192. Threaded proximal shaft 191 is configured for insertion at least partially into one of the leg receiving apertures 122, 124, 126 of body portion 110 of manipulation device 120b (see FIGS. 2A-2D). Threaded proximal shaft 191 further includes an adjustment ring 193 threadingly engaged thereabout that is rotatable to translate along and relative to threaded proximal shaft 191 such that, as will be described in greater detail below, fine adjustment of the tension on cable 181 can be achieved. Spherical distal head 192, on the other hand, functions as the first link of the articulatable segment 194 of articulatable leg 180, which will be described below.

The articulatable segment 194 of articulatable leg 180, as shown in FIGS. 5A-5B and 10A-11B, includes a plurality of alternating male and female linkages 195, 198, respectively, that are disposed about cable 181, i.e., each male and female linkage 195, 198 includes a lumen through which cable 181 extends, and are interdisposed between base member 190 and distal connector 185. The exact number of male and female linkages 195, 198, respectively, may depend on the length of cable 181. As can be appreciated, the length of cable 181 may be varied depending on a desired length of the articulatable leg 180. Thus, the various articulatable legs 180 of manipulation device 120b may define various different lengths, depending on a particular purpose.

With continued reference to FIGS. 5A-5B and 10A-11B, male linkages 195 each include a base 196 and a spherical shaped head 197, while female linkages 198 each include a substantially closed end 199a (other than the lumen defined therethrough to permit passage of cable 181) and an open end 199b that is configured to provide access to the interior of the female linkage 198. The spherical shaped head 197 of each male linkage 195 is configured for insertion into and positioning within the open end 199b of the respective adjacent female linkage 198. In the unlocked condition of articulatable leg 180, wherein cable 181 is substantially un tensioned, the spherical shaped heads 197 of the male linkages 195 are freely articulatable relative to and within the respective adjacent female linkages 198 such that articulatable segment 194 may be maneuvered and/or manipulated in any direction, i.e., 360 degrees, to define any suitable configuration. In the locked condition, on the other hand, wherein cable 181 is substantially tensioned, the spherical shaped heads 197 of the male linkages 195 are urged further into the open ends 199b of the adjacent female linkages 198 and into contact with the interior surface thereof such that the male linkages 195 and female linkages 198 are frictionally retained in fixed position relative to one another, thus fixing the configuration of articulatable segment 194 of articulatable leg 180.

Referring now to FIGS. 1-2D and 4-11B, the assembly, use, and operation of manipulation device 120b is described. In order to assembly manipulation device 100, the threaded proximal shaft 191 of the base member 190 and the proximal end 182a of the cable 181 of each articulatable leg 180 is inserted through one of the leg receiving apertures 122, 124, 126 defined through base 112 of body portion 110 of manipulation device 120b such that a pair of opposed articulatable legs 180 extend at least partially into each of the cylindrical volumes 123, 125, 127 extending through body portion 110. As can be appreciated, a desired combination of articulatable legs 180, e.g., legs 180 of varying size and/or configuration, may be engaged to body portion 110, depending on a particular purpose.

Next, a cam lock member 160 is inserted into each of the intersecting volumes 133, 135, 137 defined by cam lock member receiving passages 132, 134, 135, respectively, and is engaged to the pair of opposed articulatable legs 180 corresponding thereto, e.g., via snap fitting or otherwise engaging end rods 183 within longitudinal slots 168, 170. Once each cam lock member 160 is engaged to the corresponding pair of opposed articulatable legs 180, cover 118 may be positioned about base 112 and handle portion 140 may be engaged to body portion 110 via screws 143, 145 such that base 112, cover 118 and handle portion 140 are securely engaged to one another. Upon engagement of body portion 110 and handle portion 140, cam lock members 160 are rotatably engaged within body portion 110 by the engagement of proximal and distal caps 164, 166, respectively, within the open ends 132a and 132b, 134a and 134b, 136a and 136b of cam lock member receiving passages 132, 134, 136. Further, at this point, cam lock members 160 remain disposed in the unlocked position, corresponding to the unlocked condition of articulatable legs 180, wherein cables 181 are substantially un-tensioned. Articulatable legs 180 are biased towards this unlocked condition since cable 181 is naturally biased towards an un-tensioned state. The bias of cable 181 toward the un-tensioned state, in turn, biases cam lock members 160 toward the unlocked position.

With manipulation device 120b assembled and with articulatable legs 180 disposed in the unlocked condition, manipulation device 120b is ready for use. In use, a plurality of surgical instruments, e.g., rod reduction devices 200 and/or manipulators 300, are engaged within distal connectors 185 of articulatable legs 180. More specifically, each surgical instrument is inserted into the bushing 189 disposed within the lumen 188 of one of the distal connectors 185 and is frictionally engaged (or otherwise engaged) therein to fix the surgical instrument and distal connector 185 in position relative to one another. The surgical instruments, in turn, are coupled to bone screws 400 disposed within the vertebrae "V" (or are coupled to other anatomical structures or surgical instruments, depending on the specific procedure to be performed) either prior to or subsequently of engaging the instruments to the articulatable legs 180.

Once the surgical instruments, e.g., rod reduction devices 200 and/or manipulators 300, are engaged within the distal connectors 185 of articulatable legs 180 and are coupled to the vertebrae "V" via bone screws 400, the surgical instruments may be manipulated and/or maneuvered relative to one another and to body portion 110 of manipulation device 120b to define any suitable configuration. For example, the surgical instruments may be manipulated and/or maneuvered so as to align, or re align the vertebrae "V" in a desired configuration. As can be appreciated, manipulating and maneuvering each of the surgical instruments relative to one another and to manipulation device 120b is permitted at this point since articulatable legs 180 are disposed in the unlocked condition. Thus, as the surgical instruments are manipulated and/or maneuvered, the male and female linkages 195, 198, respectively, of the articulatable legs 180 are articulated relative to one another, allowing each of the articulatable legs 180 to form any suitable configuration.

Once the desired position of each of the surgical instruments has been achieved, e.g., once the vertebrae "V" are properly aligned with one another, one or more of the articulatable legs 180 can be locked such that the one or more articulatable legs 180 are fixed in the desired position relative to one another and to manipulation device 100. As can be appreciated, since there are multiple cam lock members 160, each corresponding to a pair of articulatable legs 180, legs 180 may be selectively locked in separate steps, e.g., a first pair, or set of legs 180 may be manipulated into position and locked, followed by a second pair, or set of legs 180 being manipulated into position and locked, etc.

In order to lock a pair of opposed articulatable legs 180 in fixed position, an engagement tool (not shown) is engaged within the engagement recess 165 defined within the corresponding cam lock member 160 and is rotated to thereby rotate the cam lock member 160 relative to body portion 110 of manipulation device 120b from the unlocked position to the locked position. As the cam lock member 160 is rotated, the cables 181 of the opposed articulatable legs 180 coupled thereto are at least partially wound up about body 162 of cam lock member 160 (and are disposed at least partially within transverse slots 172, 174), thereby tensioning the cables 181. Upon tensioning of cables 181, the spherical shaped heads 197 of the male linkages 195 are urged into frictional engagement within the adjacent female linkages 198, thus fixing the configuration of those articulatable legs 180 and transitioning those articulatable legs 180 from the unlocked condition to the locked condition. Further, as mentioned above, upon rotation of cam lock member 160 to the locked position, opposed flanges 176, 178 may be engaged within corresponding internal slots (not explicitly shown) defined within body portion 110 of manipulation device 120b such that cam lock member 160 is retained the locked position and, thus, such that the articulatable legs 180 coupled thereto are retained the locked condition.

If the tension on the cable 181 of any of the articulatable legs 180 is not suitable (e.g., if the tension is either too great or insufficient), the adjustment ring 193 threadingly engaged about the threaded proximal shaft 191 of the base member 190 of that particular articulatable leg 180 may be rotated to translated the adjustment ring 193 along the threaded proximal shaft 191, thereby increasing or reducing the tension on the cable 181. Specifically, if greater tension is desired, attachment ring 193 is rotated such that attachment ring 193 is translated proximally along threaded proximal shaft 191. Since attachment ring 193 is inhibited from passing through the leg receiving aperture 122, 124, 126, in order to permit proximal translation of attachment ring 193 along threaded proximal shaft 191, threaded proximal shaft 191 is pulled at least partially out of body portion 110 of manipulation device 100, thereby increasing the tension on cable 181. On the other hand, if it is desired to reduce the tension on the cable 181, attachment ring 193 is rotated in the opposite direction such that attachment ring 193 is translated distally along threaded proximal shaft 191, thereby allowing a greater portion of threaded proximal shaft 191 to extend into body portion 110 of manipulation device 100. As this occurs, the tension on cable 181 is reduced. As can be appreciated, adjustment ring 193 is provided for fine tune adjusting only, as it is the rotation of cam lock member 160 between the unlocked and locked positions which substantially tensions or substantially un-tensions cable 181.

With articulatable legs 180 disposed in the locked condition, thus retaining the surgical instruments engaged thereto in fixed position relative to one another, handle portion 140 of manipulation device 120b may be manipulated to move the surgical instruments and, thus, the vertebrae "V" engaged thereto, as a single unit. Alternatively or additionally, with each of the vertebrae "V" retained in fixed position relative to one another, one or more of the surgical instruments may be operated, e.g., rod reduction devices 200 and/or manipulators 300 may be operated, as described above, to engage the spinal rod 90 (FIG. 12B) within each of the aligned bone screws 400. As can be appreciated, the installation of the spinal rod 90 is facilitated by the fact that the bone screws 400 are retained in a desired position relative to one another by manipulation device 100. This advantage may also be realized in a variety of other surgical procedures where it is desired to fix one or more objects in a desired configuration relative to one another and/or to move one or more objects as a single unit.

In order to unlock any or all of the articulatable legs 180, the engagement tool (not shown) is engaged within the engagement recess 165 defined within the appropriate cam lock member(s) 160 and is rotated in the opposite direction to thereby rotate the cam lock member 160 relative to body portion 110 of manipulation device 120b from the locked position back to the unlocked position to unlock the articulatable legs 180 coupled to that cam lock member 160. With the articulatable legs 180 disposed in the unlocked condition, the articulatable legs 180 may once again be articulated to assume any suitable configuration.

The presently disclosed surgical system 10 is also usable with other bone fasteners other than the previously disclosed bone screw 400 (FIG. 1). Other suitable bone fasteners or bone screws that are usable with the presently disclosed surgical system 10 are disclosed in U.S. Pat. No. 5,733,286; U.S. Patent Application Publication No. 2010/0262196; and International Application No. PCT/US2011/048573, filed on Aug. 22, 2011. Each of these publications is hereby incorporated by reference herein in their entirety.

One suitable bone screw 50, as disclosed in U.S. Pat. No. 5,733,286, is illustrated in FIGS. 12A and 12B. The bone screw 50 includes a bowl shaped head. The bone screw 50 has a threaded shaft 52 and a curvate head 54. The curvature of the undersurface 56 of the head 54 is convex and may be a curvature of constant radius. The inner surface 58 of the head 54 is concave and may also have a constant radius of curvature. In addition, the head 54 includes a central, axial hole 60 formed in the base of the head 54 of the screw 50 which permits a screwdriver tool so that the screw 50 may be easily driven into a spinal bone.

A coupling element 80 is provided with a hemispherical insert 82 positioned in an axial bore 88 and retained by a pair of internally directed flange elements 83. The hemispherical insert 82 has an underportion 86 which is convexly hemispherical and also includes through hole such that a screw-driving tool may be inserted therethrough so that it may access the hole 60 in the head 54 of the screw 50. The relative position of the hemispherical insert 82 and the flanges 83 are provided such that the head 54 of the screw 50 may rotate polyaxially. The coupling element 80 also includes a substantially tubular rod receiving channel 89. The interior of the top portion includes a threading 72 for receiving a set screw 70. The lower portion of the axial bore 89 includes a curvate taper 84 which may have the identical radius of curvature of the undersurface 56 of the head 54 of the screw 50. The radius of curvature of the undersurface 86 of the hemispherical insert may be equal to the radius of curvature of the top surface 58 of the head 54 of the screw 50. The bottom opening of the axial bore 88 is larger than the shaft 52 of the screw 50, but is less than the diameter of the head 54, so that the head can be nested in the bottom of the bore 88, with the undersurface 56 of the head 54 slidably nested against the tapered interior surface 84 of the bore.

As seen in FIG. 12B, the assembly is locked together with a rod 90 in the channel 89 of the coupling element 80. Once the screw 50 and the coupling element 80 have been assembled, the surgeon may align the hole in the hemispherical insert 82 and the hole 60 in the head 54 and drive the assembly into the spinal bone of the patient. Removal of the screw driving tool releases the coupling element 80 to rotate freely on the head 54 of the screw 50, constrained only by the shaft 102 of the screw 50 contacting the surface 136 of the bottom of the bore 88 at the extreme range of the rotation. The head 54 of the screw also floats beneath the undersurface 86 of the hemispherical insert 82. Once the surgeon has properly positioned the coupling element 80, the rod 90 is placed in the channel 89, and seated against the top of the hemispherical insert 82. The subsequent insertion and tightening of the set screw 70 downward onto the rod 90 causes the rod 90 to compress against the hemispherical insert 82, and in turn, compresses the head 54 of the screw 50 against the tapered inner surface 84 of the bore 88. The geometry of the assembly permits secure locking of the head 54 in the bore 50 independent of the angle the coupling element 80 has been polyaxially rotated to relative to the screw 50. The assembly is thereby securely locked in position.

Another suitable bone screw for use with the presently disclosed surgical system 10 is illustrated in FIGS. 13A and 13B. A pedicle screw construct 120a includes a pedicle or bone screw 50a, a pin 44, an outer housing or coupling 42, and an inner housing or collet 40. The coupling 42 includes an annular body portion having an opening extending axially therethrough. Additionally, the coupling 42 includes a plurality of fingers 46 that are located in opposing regions of the coupling 42 and define a saddle having a generally U-shaped configuration. The u-shaped saddle is configured and dimensioned for receiving the spinal rod 90 (FIG. 12B). The collet 40 has a generally cylindrical body portion with an opening extending axially therethrough. A pair of upstanding wings 48 defines a saddle having a generally U-shaped configuration that is configured and dimensioned for receiving the spinal rod 90. The body portion includes a slot that extends from the nadir of the saddle towards the bottom of the body portion and essentially bisects the body portion along a central axis, thereby defining left and right sections of the body portion. This arrangement permits each of the wings 48 to flex towards and away from each other. The dimensions of the saddle vary according to the flexure of the wings 48. As the wings 48 are moved closer to each other, the saddle decreases in size and when the wings 48 are moved away from each other, the saddle increases in size. Allowing the saddle to vary in size permits the collet 40 to accommodate spinal rods having differing outside diameters. Compressing the wings 48 towards each other increasingly engages the outer surface of a spinal rod located in the saddle, thereby frictionally securing the rod in a desired position.

The pedicle screw 50a includes a shank 52a having a helical thread 53a formed thereon. A cutting portion 55a is formed at a distal end of the pedicle screw 50a. A head 54a is located at a proximal end of the pedicle screw 50a. The head 54a includes a plurality of grooves formed thereon and has an outer diameter that is greater than the outer diameter of the shank 52a. On the top surface of the head 54a, a recess is formed with a six-pointed star configuration for receiving the operative end of a suitable driving tool, but it is contemplated that other configurations may be used. A neck 57aa extends between a bottom surface of the head 54a and the beginning of the helical thread 53a. As configured, the neck 57a is unthreaded. As shown, at least a portion of the diameter of the neck 57a is less than the diameter of the bottom of the head 54a and the major diameter of the threaded portion of the shank 52a. The collet 40 is seated atop the head 54s of pedicle screw 50a. The opening at the bottom of collet 40 is dimensioned and configured for receiving the head 54a. As such, the collet 40 and the head 54a are rotatable and pivotable in relation to each other, thereby allowing the pedicle screw 50a to be repositioned in a plurality of orientations relative to the collet 40. The combination of the collet 70 and pedicle screw 10 is inserted into the coupling 50. The pin 44 aligns the collet 40 and the coupling 42 for maintaining a fixed relationship between them. As assembled, the pedicle screw 50a is rotatable and pivotable in relation to the collet 40 and the coupling 42.

Figure 14A:
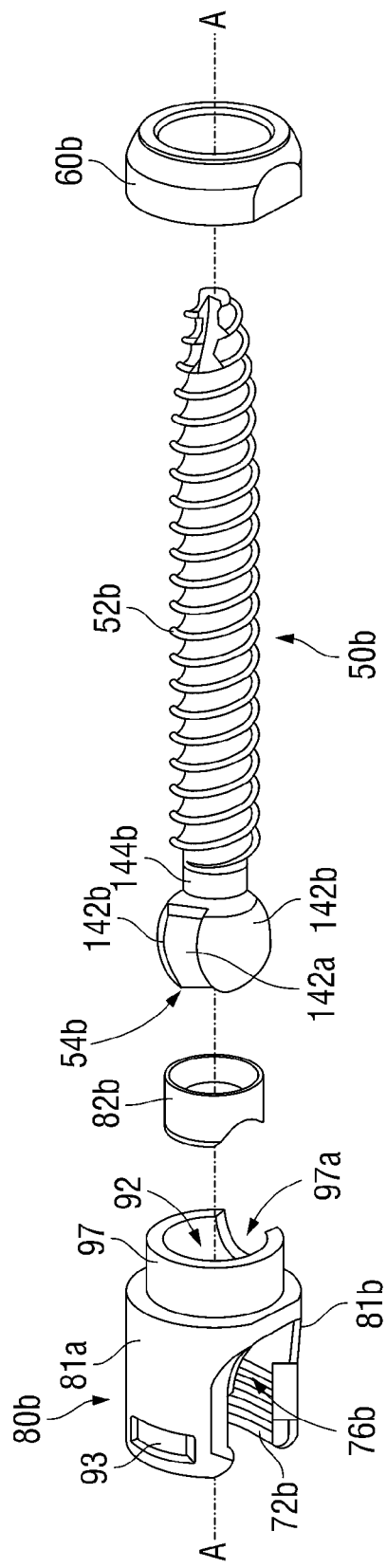
FIG. 14A is an exploded, perspective view of another embodiment of a bone screw usable with the presently disclosed surgical systems.
Figure 14B:
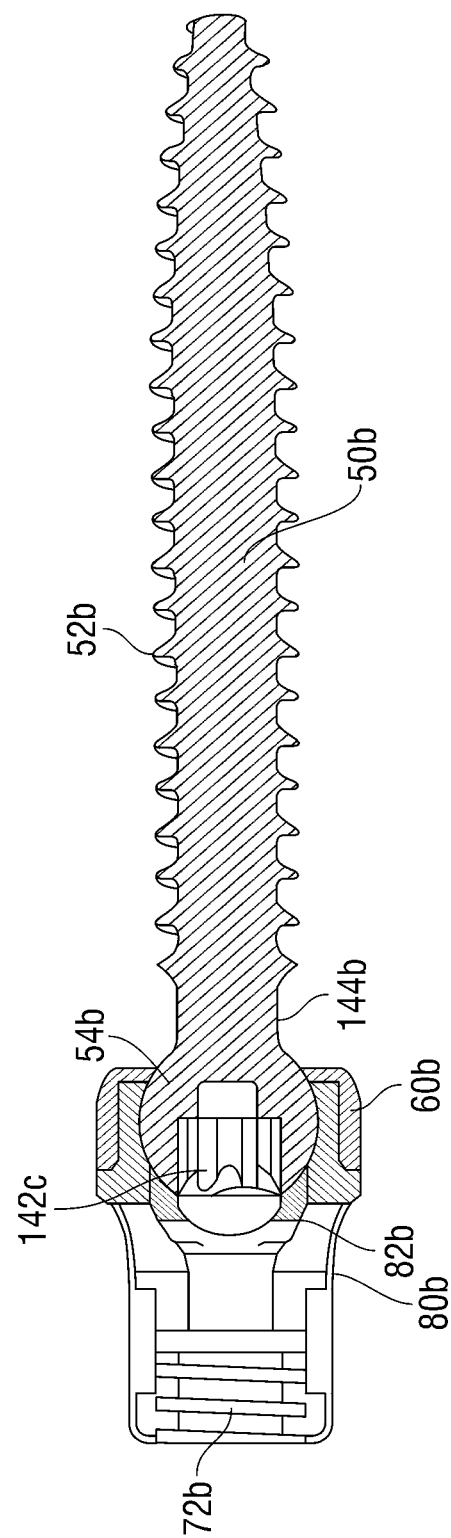
FIG. 14B is a side, cross-sectional view of the bone screw of FIG. 14A.

Another bone screw usable with the surgical system 10 is shown in FIGS. 14A and 14B. A bone screw construct 120b includes a housing 80b, a cap 60b, a bone screw 50b, and a set screw 70 (FIG. 12B). The housing 80b defines an opening therethrough that permits the reception of any suitable driving instrument (not shown) therethrough. The housing 82b includes opposing walls 81a, 81b that define a U-shaped channel therebetween. Each opposing wall 81a, 81b includes an external flanged recess 93 that is configured to facilitate grasping of the housing 80b by an instrument, such as rod reduction device 200 (FIG. 1) that can also be used to facilitate insertion of the bone screw construct 120b into a pedicle of a vertebral body. The internal surfaces of opposing walls 81a, 81b include threaded portions 72b that are threadably engagable with external threads of the set screw 70 (FIG. 12B) and facilitate securing the spinal rod 90 (see FIG. 12B) within the channel of the housing 80b adjacent the anvil 82b.

The housing 80b includes a collar 97 extending therefrom. The collar 97 may have a smaller diameter than the diameter defined by the opposing walls 81a, 81b of the housing 80b. The collar 97 facilitates attaching the cap 60b to the housing 80b once the bone screw 50b is secured to the housing 80b. The collar 97 has a cut out 97a that provides a recess for the reception of a portion of the bone screw 50b, namely a neck 144b of the bone screw 50b. The bone screw 50b includes a head 54b and a threaded shaft 52b extending from the head 54b. The bone screw 50b may be a self-starting fastener or self-tapping fastener. The head 54b is selectively securable within the housing 80b and includes a first portion 142a and a second portion 142b. The head 54b includes a driving recess 142c, which may be hexolobular or any other suitable configuration, defined in a proximal surface of the head 54b. The driving recess 142c is engagable with any suitable driving instrument (not shown) to enable the driving instrument to advance the bone screw 50b within bone. The first portion 142a, which may have substantially cylindrical surfaces (but any suitable shape is contemplated), enables the head 54b to fit through the opening 92 defined in the housing 80b from the distal end of the housing 80b. In particular, opposed cylindrical surfaces of the first portion 142a may be positioned in co-axial alignment transverse to axis "A" (simultaneously, the opposed spherical surfaces of the second portion 142b are coaxial with axis "A") of the opening 92 (while the shaft 52b is perpendicular to axis "A" by virtue of the neck 144b being seated in cut out 97a) to enable the head 54b to securably fit into housing 80b upon the rotation of the shaft 52b into coaxial alignment with axis "A.". The second portion 142b, which may have substantially spherical surfaces (but any suitable shape is contemplated), maintains the head 54b of the bone screw 50b within the housing 80b once the head 54b is fully inserted from the distal end of the housing 80b as discussed above.

It will be understood that various modifications may be made to the embodiments of the present disclosure. Therefore, the above description should not be construed as limiting, but merely as exemplifications of embodiments. Those skilled in the art will envision other modifications within the scope and spirit of the present disclosure.

What is claimed is:

1. A manipulation device, comprising:
    a body portion;
    a handle portion including a pair of supports configured to engage the body portion;
    a plurality of articulatable legs extending from the body portion, each of the articulatable legs configured to engage a surgical instrument at a distal end thereof, each of the articulatable legs transitionable between an unlocked condition, wherein the articulatable leg is free to articulate, and a locked condition, wherein the articulatable leg is fixed in position;
    at least one lock member operably disposed within the body portion and coupled to at least one of the articulatable legs, the lock member rotatable relative to the body portion between an unlocked position and a locked position for transitioning the at least one articulatable leg coupled thereto between the unlocked condition and the locked condition;
    at least one manipulator frictionally engaged with a proximal end of one leg of the plurality of articulatable legs, the at least one manipulator configured for selective engagement with a pedicle screw; and
    at least one rod reduction device including an elongated extension tube extending proximally therefrom, the at least one rod reduction device and elongated extension tube are frictionally engaged to a proximal end of one leg of the plurality of articulatable legs, the at least one rod reduction device configured for selective engagement with a spinal rod and a pedicle screw.

2. The manipulation device according to claim 1, wherein the lock member is coupled to a pair of articulatable legs such that rotation of the lock member between the locked position and the unlocked position transitions both articulatable legs of the pair between the unlocked condition and the locked condition.

3. The manipulation device according to claim 1, wherein each articulatable leg includes:
    a cable coupled to the lock member at a proximal end thereof; a distal connector coupled to the cable at a distal end thereof, the distal connector configured to engage a surgical instrument therein; and
    a plurality of alternating male and female linkages, the male and female linkages disposed about the cable between the proximal and distal ends thereof 4. The manipulation device according to claim 3, wherein the cable is transitionable between a substantially untensioned state and a substantially tensioned state to transition the articulatable leg between the unlocked condition and the locked condition.

5. The manipulation device according to claim 4, wherein, in the substantially untensioned state, the alternating male and female linkages are free to articulate relative to one another and wherein, in the substantially tensioned state, the alternating male and female linkages are retained in fixed position relative to one another.

6. The manipulation device according to claim 4, wherein each articulatable leg further includes an adjustment ring coupled thereto, the adjustment ring selectively rotatable relative to the articulatable leg to vary the tension on the cable.

7. The manipulation device according to claim 1, wherein manipulating the handle portion results in corresponding movement of the body portion.

8. The manipulation device according to claim 1, wherein the lock member includes an engagement recess defined therein that is configured to receive a complementary engagement tool for rotating the lock member between the unlocked position and the locked position.

9. The manipulation device according to claim 1, wherein the body portion includes at least one compression relief slot defined therein.

10. The manipulation device according to claim 1, wherein the pair of supports are configured to releasably engage with the body portion.

11. The manipulation device according to claim 1, wherein the handle portion includes a pair of spaced apart handle members.

12. The manipulation device according to claim 11, wherein the spaced apart handle members are releasably engageable with the pair of supports.

13. The manipulation device according to claim 1, wherein the manipulation device is capable of being manipulated in all six degrees of freedom relative to the at least one manipulator and the at least one rod reduction device when a corresponding pair of articulatable legs are in an unlocked position.

14. The manipulation device according to claim 1, wherein the manipulation device is capable of being rigidly supported in all six degrees of freedom by the at least one manipulator and the at least one rod reduction device when a corresponding pair of articulatable legs are in a locked position.

15. The manipulation device according to claim 1, wherein at least one leg of the plurality of articulatable legs is disposed on a first side the body portion and at least one other leg of the plurality of articulatable legs is disposed on a second side of the body portion.

16. A surgical system, comprising:
a manipulation device, including:
a body portion;
a handle portion including a pair of supports configured to engage the body portion;
a plurality of articulatable legs extending from the body portion, each of the articulatable legs transitionable between an unlocked condition, wherein the articulatable leg is free to articulate, and a locked condition, wherein the articulatable leg is fixed in position; and
at least one lock member operably disposed within the body portion and coupled to at least one of the articulatable legs, the lock member rotatable relative to the body portion between an unlocked position and a locked position for transitioning the at least one articulatable leg coupled thereto between the unlocked condition and the locked condition; and at least one manipulator engaged to at least one leg of the plurality of articulatable legs, and at least one rod reduction device engaged with at least one other leg of the plurality of articulatable legs, wherein, in the unlocked condition, the at least one manipulator and at least one rod reduction device are manipulatable independently of one another and wherein, in the locked condition, the at least one manipulator and at least one rod reduction device are manipulatable in coordination with one another.

17. The surgical system according to claim 16, wherein the pair of supports are configured to releasably engage with the body portion.

18. The surgical system according to claim 16, wherein the handle portion includes a pair of spaced apart handle members.

19. The surgical system according to claim 18, wherein the spaced apart handle members are releasably engageable with the pair of supports.

20. The surgical system according to claim 16, wherein at least one leg of the plurality of articulatable legs is disposed on a first side the body portion and at least one other leg of the plurality of articulatable legs is disposed on a second side of the body portion.

* * * * *